United States Patent [19]

Moussy

[11] Patent Number: 5,534,025
[45] Date of Patent: Jul. 9, 1996

[54] VASCULAR BIOARTIFICIAL ORGAN

[75] Inventor: Francis Moussy, Edmonton, Canada

[73] Assignee: The Governors of the University of Alberta, Edmonton, Canada

[21] Appl. No.: 257,120

[22] Filed: Jun. 8, 1994

[30] Foreign Application Priority Data

Jun. 8, 1993 [GB] United Kingdom .................. 9311784

[51] Int. Cl.⁶ .................................................. A61F 2/04
[52] U.S. Cl. ............................. 623/11; 623/12; 424/424
[58] Field of Search ............................ 623/11, 12; 604/4, 604/5, 6, 892.1; 435/240.22; 424/424, 425

[56] References Cited

U.S. PATENT DOCUMENTS

| | | | |
|---|---|---|---|
| 4,756,705 | 7/1988 | Beijbom et al. ......................... | 604/4 |
| 5,002,661 | 3/1991 | Chick et al. .............................. | 604/4 |
| 5,192,320 | 3/1993 | Anazawa et al. ........................ | 623/12 |
| 5,387,237 | 2/1995 | Fournier et al. ........................ | 623/11 |

FOREIGN PATENT DOCUMENTS

| | | | |
|---|---|---|---|
| 9403126 | 2/1994 | WIPO ...................................... | 623/11 |
| 9418906 | 9/1994 | WIPO ...................................... | 623/11 |

Primary Examiner—David H. Willse
Assistant Examiner—Bruce E. Snow
Attorney, Agent, or Firm—Dinsmore & Shohl

[57] ABSTRACT

A bioartificial organ is provided which is inserted as an anastomosis between an artery and a vein. Blood flowing through the fluid conduits of the device is separated by a semi-permeable membrane from a chamber containing living cells or tissue.

9 Claims, 3 Drawing Sheets

VASCULAR BIOARTIFICIAL ORGAN

This invention relates to artificial organs and more particularly to vascular bioartificial organs.

BACKGROUND OF THE INVENTION

A variety of attempts have been made to replace or supplement the function of failing mammalian organs with artificial organs. In bioartificial organs, actual organ tissue or cells are incorporated into the artificial device and the device is located in vivo in a situation such that the organ tissue or cells are exposed as much as possible to normal physiological signals.

In a typical bioartificial organ, the transplanted tissue is protected against immune rejection by a semi-permeable membrane permeable to nutrients, oxygen, stimulating molecules and the secreted active molecules but not to immunoglobulins. Because the semi-permeable membrane prevents an attack by the immune system, tissue from other species can be used, thus allowing for an almost unlimited source of tissue. In addition, immunosuppressant drugs are not necessary. The porosity of the membrane must be adjusted to selectivity allow the passage of the suitable molecules but not immunoglobulins. This can be achieved with membranes having a molecular weight cut off inferior to 100,000 daltons which excludes larger molecules such as immunoglobulins (>160,000 daltons).

This approach is applicable for the treatment of various illnesses such as hemophilia, hypoparathyroidism, Parkinson's disease, Huntington's disease and hepatic failure.

One disease which has been the focus of this approach is diabetes, a disease caused by the destruction of the insulin-secreting β cells of the Islets of Langerhans in the pancreas and affecting about 30 million people worldwide.

The usual therapy for diabetes is daily insulin injections during the entire life of the patient. As well as being a cumbersome therapy, insulin injections do not achieve optimal control of glycemia. It is thought that the long-term complications of diabetes, which occur even with insulin therapy, are related to this imperfect control of glycemia.

If insulin could be supplied to a diabetic patient by living β cells which are capable of responding in a finely tuned manner, so as to keep blood sugar within normal limits, an improved outlook for diabetic patients could be expected.

Various attempts have been made to incorporate islet cells into an artificial pancreas device or bioartificial pancreas.

Healthy islet cells are separated from host tissues in such devices by a semi-permeable membrane which is permeable to glucose and insulin but not to cells or immunoglobulins. This protection of the islet graft by the membrane eliminates the need for immunosuppression of the patient.

Another benefit derived from the use of the membrane is that it allows for the use of xenogeneic islets, such as porcine islets, thus reducing the problem of the limited availability of transplantable human pancreatic tissue.

Bioartificial pancreases can be divided into two groups: the first group comprises extravascular systems, where there is no contact between the protective membrane and blood of the patient. The second group comprises vascular systems where the blood of the patient circulates in contact with the membrane.

One example of the second group is the bioartificial pancreas described by Lapeintre, J. et al., (1990), Artificial Organs, v. 14, pp. 20–27. This device is U-shaped in design and is connected to an arteriovenous shunt.

Glucose and insulin transfer through the membrane is achieved in this device by two types of flux; a flux by diffusion caused by the glucose and insulin concentration gradients between the blood and the islet compartment, and a flux by ultrafiltration caused by the difference of pressure between the upper blood channel and the lower blood channel of the device. This difference of pressure is achieved by the resistance to blood flow in a small diameter U-shaped tube connecting the two blood channels. Therefore, in this system, a resistance to flow is required to obtain an ultrafiltration flux. However, this resistance to flow creates serious blood clotting problems in this device, making the device unsuitable for in vivo implantation.

In order to avoid blood clotting, the blood flow through the device should be without any resistance to flow. In addition, the blood channels of this device are designed as flat, rectangular chambers with grooved passages, which is not a desirable design for use with blood. These channels should preferably be designed so as to avoid turbulence and stasis of the blood flow.

These problems have been overcome by the bioartificial organ of the present invention which utilizes the natural pressure difference between artery and vein (~80 to 90 mm Hg), to create a large ultrafiltration flux through the islet chamber, instead of using a pressure difference artificially induced by creating a large resistance to blood flow. In addition, this new device minimizes the extent of artificial surface in contact with blood and does not introduce resistance or disruption in the blood flow that would induce the turbulence responsible for blood clotting.

SUMMARY OF THE INVENTION

A bioartificial device is provided for replacing or supplementing the function of a mammalian organ comprising a first fluid conduit having inlet means and outlet means for connection into a first blood stream and having a wall portion comprising a first semi-permeable membrane;

a second fluid conduit having inlet means and outlet means for connection into a second blood stream and having a wall portion comprising a second semi-permeable membrane;

said first and second fluid conduits being sealingly secured together with said semi-permeable membranes opposed and spaced apart to form a chamber therebetween for receiving cells or tissue of the organ to be replaced or supplemented.

A bioartificial pancreas is provided comprising an arterial blood channel having inlet means and outlet means for connection into an arterial blood stream and having a wall at least a portion of which comprises a first semi-permeable membrane; and a venous blood channel having inlet means and outlet means for connection into a venous blood stream and having a wall at least a portion of which comprises a second semi-permeable membrane;

said first and second fluid conduits being sealingly secured together with said semi-permeable membranes opposed and spaced apart to form a chamber therebetween for receiving cells or tissue of the organ to be replaced or supplemented.

SUMMARY OF THE DRAWINGS

Certain embodiments of the invention are described, reference being made to the accompanying drawings, wherein.

DETAILED DESCRIPTION OF THE INVENTION

The invention provides a novel and convenient bioartificial device for replacing or supplementing the function of a deficient mammalian organ.

The device comprises two fluid conduits, connectable into a first and second bloodstream respectively. Each fluid conduit has a wall portion comprising a semi-permeable membrane which permits passage of molecules of interest into and out of the bloodstream to which the conduit is connected, while preventing the passage of large molecules such as immunoglobulins.

The two fluid conduits are sealingly secured together with their semi-permeable membrane wall portions opposed and spaced apart to form a chamber between the two semi-permeable membranes. Cells or tissue from the organ whose function is to be supplemented or replaced are placed in this chamber. The conduits may be sealingly secured together by any suitable means, so that the chamber formed between the membranes is fluid-tight other than across the semi-permeable membranes.

The device is inserted between an artery and a vein and forms an anastomosis between the two.

One embodiment of the device of the invention is shown in FIGS. 1 to 6.

Figure 2:
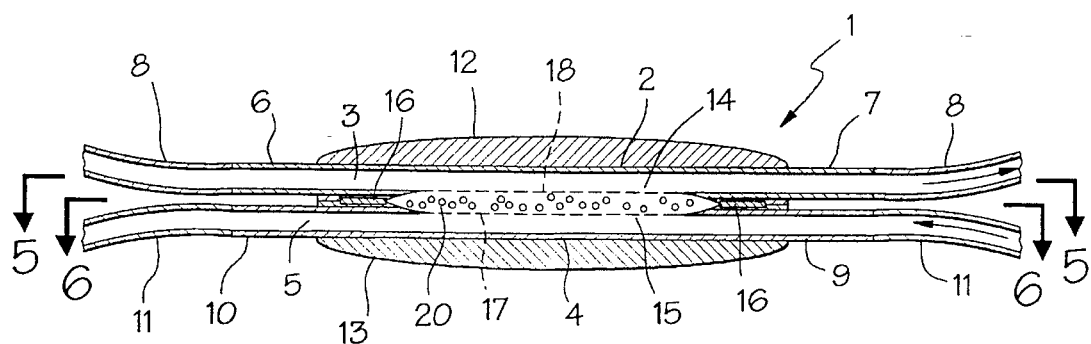
FIG. 2 shows a sectional view of the device of FIG. 1 through line 2—2.
Figure 3:
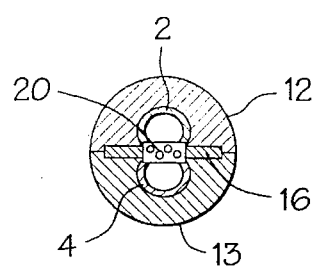
FIG. 3 shows a sectional view of the device of FIG. 1 through line 3—3.

As seen in FIG. 2, the device 1 comprises a first fluid conduit 2 which forms an arterial blood channel of the device and a second fluid conduit 4 which forms a venous blood channel 5 of the device. Fluid conduit 2 has inlet means 6 and outlet means 7 for connection into an artery 8 and fluid conduit 4 has inlet means 9 and outlet means 10 for connection into a vein 11.

Support members 12 and 13 comprise blocks of suitable material having a flat surface into each of which is drilled a groove for housing one of the fluid conduits 2 and 4.

Fluid conduits 2 and 4 have apertures 14 and 15 in their walls.

The device is assembled by first securing fluid conduits 2 and 4 in the grooves of support members 12 and 13 respectively, with apertures 14 and 15 unobstructed.

Figure 4:
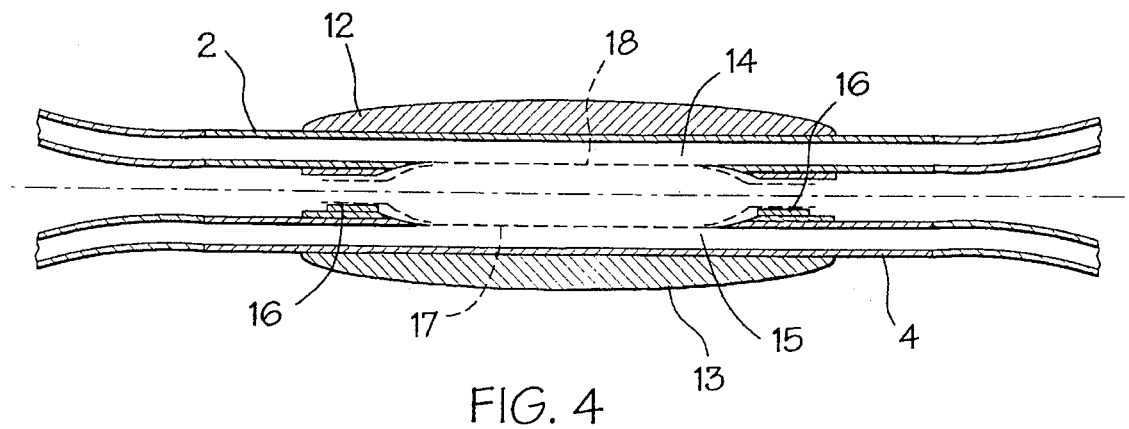
FIG. 4 shows an exploded view of the device of FIG. 2.
Figure 5:
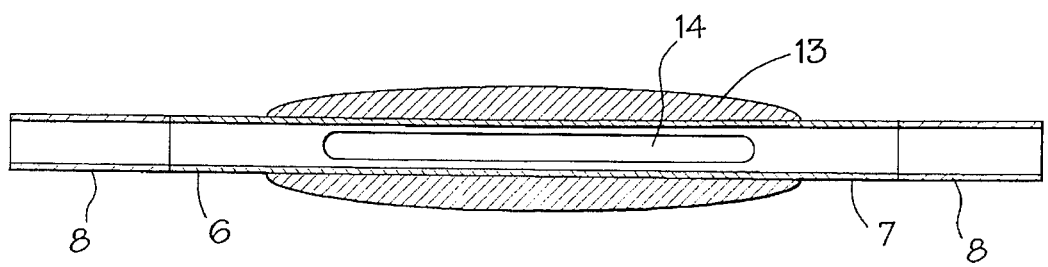
FIG. 5 shows a sectional view of the device of FIG. 2 through line 5—5.

A gasket 16 is placed on support member 13 so as to surround aperture 15. The gasket may be glued to support member 13. A first semi-permeable membrane 17 of area greater than aperture 15 is placed over gasket 16 and aperture 15 of fluid conduit 4, as seen in FIG. 4, and the desired cells or tissue are placed on membrane 17. A second semi-permeable membrane 18 is placed over membrane 17 and support member 12 and fluid conduit 2 are placed on top, with aperture 14 of fluid conduit 2 opposed to membrane 18.

Support members 12 and 13 are secured together by a clamp 19 which is tightened so that gasket 16 is squeezed between the support members and forms a fluid-tight seal surrounding chamber 20 which lies between the semi-permeable membranes and houses the cells or tissue.

The device may be assembled around the cells or tissue as described or, in accordance with a further embodiment, an inlet port may be provided through which cells or tissue may be inserted into or removed from chamber 20 after assembly of the device.

The fluid conduits may be constructed with a semi-permeable membrane as an integral part of the conduit, rather than by placing a membrane over an aperture in the conduit as described above.

The support members may be made of any suitable biocompatible and preferably lightweight material, including plastics such as polyacrylic, polycarbonate, polysulfone, polymethylacrylate or mixtures of these, stainless steel, titanium or other metals.

The fluid conduits may be made of any suitable biocompatible material which can function as an insert to an artery or vein. For example, biocompatible tubing such as silastic tubing may be employed. Especially preferred for the fluid conduits of the device are commercially available vascular prostheses, made for example of Dacron (polyester) or Gore-Tex (polytetrafluoroethylene).

Any suitable biocompatible material which will provide a fluid-tight seal may be used for the gasket.

The supporting members of the device may conveniently be secured together by clamping as described but may optionally be secured by gluing or welding.

The semi-permeable membranes should not be so thick as to reduce the ultrafiltration flux unduly. A thickness of 20 μm is preferred.

The membranes should have a molecular weight cut off such that they are permeable to the desired secretory product of the organ but should not permit passage of immunoglobulins. Membranes made of a copolymer of polyacrylonitrile, for example those developed by Hospal, France, are preferred, although other membranes of similar thickness and permeability may be employed.

The diameter of the blood channels in the device should preferably be matched to the diameter of the blood vessels to which it is to be connected (up to 1 cm). It is important to avoid a large change in diameter at the connecting site between the fluid conduits of the device and the blood vessels in order to avoid blood clotting. It is preferable that the blood channels of the device should have a diameter of not less than about 3 mm to reduce the possibility of blood clotting.

The flux of materials through the membranes depends on the depth of the chamber between the membranes in which the cells are contained. This chamber should not be more than about 5 mm in depth (distance between the two membranes); a depth of about 0.2 mm is preferred. The length of the chamber will depend on the number of cells to be accommodated.

The device of the invention is preferably constructed with a smooth surface without corners, for better implantation.

It should be an overall size suitable for implantation. A size of approximately 10 cm in length is preferred.

The size may be reduced, for example, to 2 to 3 cm, if a smaller device or only a small number of cells is required.

Alternatively, the device may be made larger, for example 10 to 20 cm, if a larger number of cells is to be used.

In accordance with a preferred embodiment of the invention, a bioartificial pancreas is provided. Membranes should have a molecular weight cut off of about 20,000 to 100,000 daltons, a cut off of about 50,000 daltons being preferred. Polyacrylonitrile membranes, AN 698 of Hospal, France are suitable. Pancreatic islets from any suitable species (for example, human, pig, dog) are placed in chamber 20 of the device.

Islets are isolated by any suitable procedure. For example, they may be isolated by enzymatic digestion of the pancreas, as described in *Pancreatic Islet Cell Transplantation*, C. Ricordi, Ed., (1992), R. G. Landes Company, Tex.

As seen in Example 1, the device provides excellent insulin secretion kinetics in response to glucose concentration in vitro. A similar response would be expected in vivo.

The device should preferably be implanted in a location where a large artery and a vein are in close proximity. For example, insertion between the femoral artery and femoral vein provides a good location. Insertion between artery and vein of the pancreas (such as the splenic artery and splenic vein) may also be used, providing a reproduction of the physiological drainage of insulin. As understood by those skilled in the art, the type of technique used for insertion of vascular prostheses may be employed for implanting the device.

Glucose and insulin are transferred across the membranes of the device by diffusion flux and by ultrafiltration flux. The ultrafiltration flux is created by the natural difference of blood pressure between the arterial and venous systems.

Arterial blood flows in the arterial blood channel of the device under high pressure, and venous blood flows in the other blood channel under low pressure. Therefore, the new geometry of the device of the invention does not introduce any resistance to flow. In addition, the blood channels in the device have a large diameter and tubular shape similar to blood vessels, reducing the likelihood of turbulence or stasis of the blood flow. Consequently, the geometry of the device of the invention is adapted to minimize problems of blood clotting.

Also, because the flux by ultrafiltration provides for good oxygenation and prevents inhibition of insulin secretion by a high insulin concentration, the islets can be packed together.

Optionally, hemocompatibility of the device can be enhanced by heparinizing the membranes (ionic or covalent binding of heparin on the membranes) or by growing endothelial cells on the fluid conduit walls after seeding with endothelial cells, to mimic the lining of blood vessels.

As will be understood by those skilled in the art, the device of the invention may be used as a substitute for a selected organ by use of the appropriate tissue cell types, for example hormone secreting cells such as parathyroid hormone-secreting cells for the treatment of hypoparathyroidism. Genetically engineered cells may also be used, for example for the treatment of haemophilia. Hepatocytes may also be used in the device to provide an artificial liver for patients with liver disease.

EXAMPLE 1

A device in accordance with the invention was constructed using polyacrylonitrile membranes (AN 698, Hospal, France) and seeded with 2000 rat islets prepared according to the method developed by Lacy PE and Kostianovski M, (1967), Diabetes, V. 16, pp. 35–41 and was tested in an in vitro system.

The supporting members of the device were made by cutting a 10 cm plexiglass rod approximately 2.5 cm diameter in half along its long axis. Along the length of the flat surface of each portion of the rod was drilled a shallow channel of a depth corresponding to the diameter of the vascular prostheses or tubing to be used to form the fluid conduits of the device. For in vitro testing, the vascular prostheses were replaced by silastic tubing, although for in vivo use, vascular prostheses are preferred. A suitable length of 6 mm internal diameter silastic tubing was attached to each supporting member by gluing it in place in the prepared channels. An aperture of area about 4 $cm^2$ was cut in each piece of silastic tubing on the side opposite the supporting member.

Figure 6:
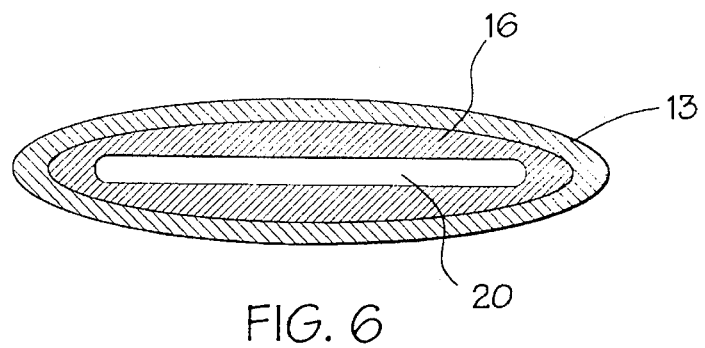
FIG. 6 shows a sectional view of the device of FIG. 2 through line 6—6.

A length of 2 mm diameter silastic tubing was used to form a gasket surrounding the aperture in one silastic fluid conduit, as seen in FIG. 6; the gasket was attached by gluing it to the flat surface of the plexiglass supporting member.

Figure 1:
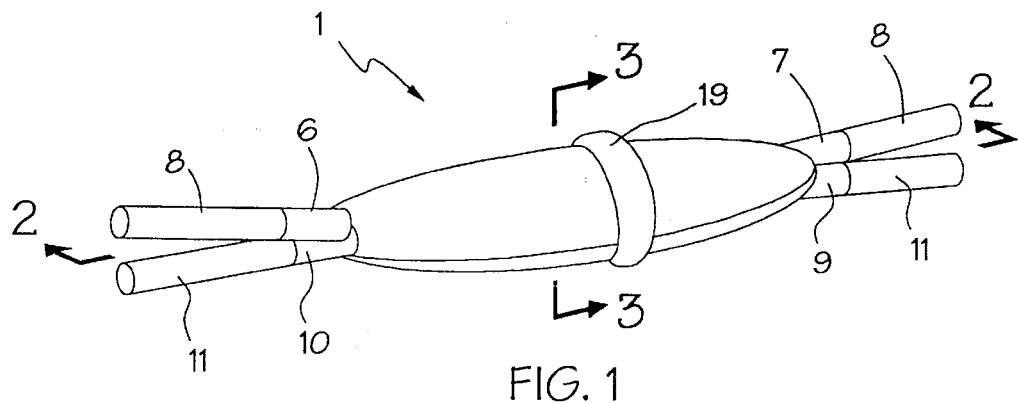
FIG. 1 shows a schematic view of a bioartificial device in accordance with one embodiment of the invention.

A polyacrylonitrile membrane (AN 693) of area slightly larger than 4 $cm^2$ was placed over the aperture and its surrounding gasket to form one wall of the semi-permeable chamber. 2000 rat islets were placed on the membrane, a second membrane was placed over the islets and the other half of the device was inverted over it with its fluid conduit aperture opposed to the second membrane. The two halves of the device were secured together by clamping with a circular clamp placed around the center of the device, as seen in FIG. 1.

Figure 7:
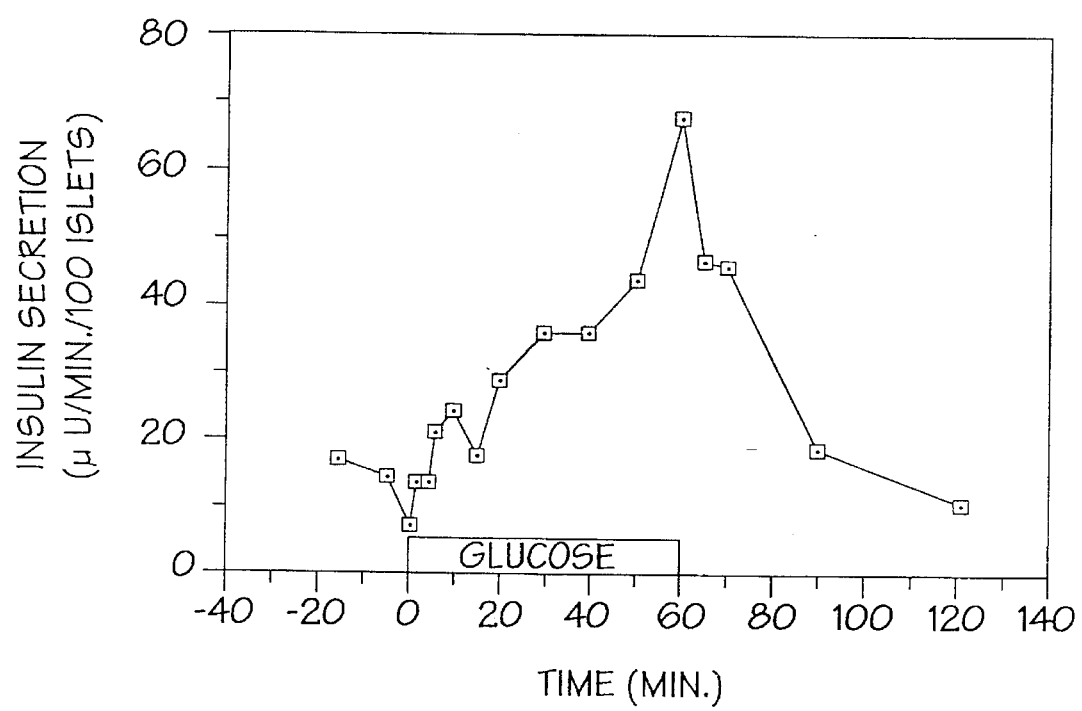
FIG. 7 shows the response to glucose of a bioartificial pancreas in accordance with the invention.

The device was perfused using a peristaltic pump with a synthetic culture medium (RPMI, Sigma supplemented with fetal calf serum and glucose) at a flow rate of 25 ml/min and a difference of pressure between the 2 channels of 100 mmHg. The culture medium was warmed to 37° C. using a waterbath and bubbled with 5% $CO_2$ and 95% $O_2$. After a one hour rinse of the system, the glucose level was increased from 2.2 mM to 27 mM for 1 hour and then decreased to 2.2 mM for another hour. The results are shown in FIG. 7.

The islets in the device produced insulin in response to glucose with excellent kinetics. Insulin secretion increased rapidly after a 1 hour square wave increase in glucose concentration from 2.2 mM to 27 mM. Insulin secretion returned to its basal level after the end of the stimulation.

The present invention is not limited to the features of the embodiments described herein, but includes all variations and modifications within the scope of the claims.

We claim:

1. A bioartificial device for replacing or supplementing the function of a mammalian organ, comprising a first fluid conduit having inlet means and outlet means for connection into a first blood stream and having a wall portion comprising a first semi-permeable membrane;

a second fluid conduit having inlet means and outlet means for connection into a second blood stream and having a wall portion comprising a second semi-permeable membrane;

first and second support members for sealingly securing said first and second fluid conduits together with said semi-permeable membranes opposed and spaced apart to form a chamber therebetween for receiving cells or tissue of the organ to be replaced or supplemented; and a gasket arranged between said first and second support members and surrounding the chamber.

2. The device of claim 1 wherein the first blood stream is an arterial blood stream and the second blood stream is a venous blood stream.

3. The device of claim 2 wherein each fluid conduit comprises a tube and the wall portion of the conduit comprising a semi-permeable membrane comprises an aperture in the tube covered by a semi-permeable membrane, and wherein said supporting members each have a groove in which the fluid conduits are supported, said members being spaced apart by said gasket and secured together by a clamp.

4. The device of claim 3 wherein the semi-permeable membranes have a porosity which permits the passage of molecules of molecular weight less than about 100,000 Daltons while retaining molecules of larger molecular weight.

5. The device of claim 4 wherein each of the first and second fluid conduits has a diameter substantially matching the diameter of the blood vessels of the blood stream into which each is connected.

6. The device of claim 5 wherein the organ whose function is to be replaced or supplemented is the endocrine pancreas.

7. The device of claim 5 further comprising an inlet port communicating with said chamber for introduction or removal of cells or tissue.

8. The device of claim 6 wherein the chamber contains pancreatic cells or islets.

9. A bioartificial pancreas device, comprising an arterial blood channel having inlet means and outlet means for connection into an arterial blood stream and having a wall portion comprising a first semi-permeable membrane;

a venous blood channel having inlet means and outlet means for connection into a venous blood stream and having a wall portion comprising a second semi-permeable membrane;

first and second support members for sealingly securing said arterial blood channel and said venous blood channel together with said semi-permeable membranes opposed and spaced apart to form a chamber therebetween for receiving cells or tissue of a pancreas to be replaced or supplemented; and a gasket arranged between said first and second support members and surrounding the chamber.

* * * * *